United States Patent [19]

Boettcher et al.

[11] Patent Number: 5,206,417
[45] Date of Patent: Apr. 27, 1993

[54] RADIATION-SENSITIVE, ETHYLENICALLY UNSATURATED COPOLYMERIZABLE COMPOUNDS AND THEIR PREPARATION

[76] Inventors: Andreas Boettcher, 38 Konrad-Adenauer-Ring, 6907 Nussloch; Gerd Rehmer, 1 Koenigsberger Strasse, 6712 Bobenheim-Roxheim, both of Fed. Rep. of Germany

[21] Appl. No.: 810,348

[22] Filed: Dec. 18, 1991

Related U.S. Application Data

[63] Continuation of Ser. No. 365,132, Jun. 12, 1989, abandoned.

[30] Foreign Application Priority Data

Jun. 16, 1988 [DE] Fed. Rep. of Germany ....... 3820463

[51] Int. Cl.$^5$ ................ C07C 269/02; C07C 271/32; C07C 271/54
[52] U.S. Cl. ..................... 560/137; 526/328; 560/133; 560/134; 560/135; 560/136
[58] Field of Search ............... 560/134, 133, 135, 136, 560/137

[56] References Cited

U.S. PATENT DOCUMENTS

| | | | |
|---|---|---|---|
| 3,214,492 | 10/1965 | Tocker | 526/329.1 |
| 3,322,818 | 5/1967 | Hanze | 560/163 |
| 3,429,852 | 2/1969 | Skoultchi | 560/205 X |
| 3,657,184 | 4/1972 | Segawa et al. | 560/163 X |
| 4,148,987 | 4/1979 | Winey | 526/316 |
| 4,504,628 | 3/1985 | Johnson | 560/163 X |
| 4,634,791 | 1/1987 | Meier et al. | 560/163 |

FOREIGN PATENT DOCUMENTS 0246848 11/1987 European Pat. Off. .
3345103 6/1985 Fed. Rep. of Germany .

OTHER PUBLICATIONS

Petersen, *Liebigs Ann. Chem.* 562, (1947), 205–229.
J. Burkus, *J. Org. Chem.* 26 (1961), 779–782.
Kay et al., *J. Chem. Soc.*, (C), 1968, 3011–3014.

*Primary Examiner*—José G. Dees
*Assistant Examiner*—Vera C. Clarke
*Attorney, Agent, or Firm*—Keil & Weinkauf

[57] ABSTRACT

The ethylenically unsaturated organic compounds are of the general formula $$R-\overset{\overset{\displaystyle O}{\|}}{C}-R^1$$

where R is alkyl, aryl or a radical $R^1$, and $R^1$ is a radical

[structure: benzene ring with substituents $R^2$, $R^3$, $R^4$, $R^5$, $R^6$]

where $R^2$ to $R^6$ are each H, alkyl, OH, Oalkyl, SH, Salkyl, halogen, N(alkyl)$_2$ or N(alkyl)(aryl), and not less than one but not more than three of the radicals $R^2$ to $R^6$ are each a radical $$-O-\underset{\underset{\displaystyle O}{\|}}{C}-NH-X-O-\underset{\underset{\displaystyle O}{\|}}{C}-\underset{\underset{\displaystyle Y}{|}}{C}=CH_2$$

where X is alkylene or oxaalkylene, each of 2 to 10 carbon atoms, and Y is H or CH$_3$. These compounds have particularly high photochemical reactivity in the medium-wavelength to relatively long-wavelength UV range.

14 Claims, No Drawings

RADIATION-SENSITIVE, ETHYLENICALLY UNSATURATED COPOLYMERIZABLE COMPOUNDS AND THEIR PREPARATION

This application is a continuation application of Ser. No. 07/365,132, filed on Jun. 12, 1989, now abandoned.

The present invention relates to novel radiation-sensitive, ethylenically unsaturated acetophenone and benzophenone derivatives and a process for their preparation.

UV-sensitive acetophenones and benzophenones are frequently added to radiation-sensitive polymers as external initiators (for example G. Li Bassi, J. Rad. Cur. 14 (1987), 18). In general, however, such procedures are not entirely satisfactory since, after the initiators have been mixed with the polymers, problems arise with the compatibility, the uniformity of distribution, the volatility, the odor and the toxicity and of exudation and migration of the additive, which frequently lead to an undesirable, premature and non-uniform reaction. During the actual process of irradiation, lower reactivity is then observed as a result of lower effective initiator concentrations.

It is known that a number of the stated problems can be solved if the radiation-sensitive initiator is copolymerized with monomers by a conventional process, ie. incorporated in a polymer chain. The photosensitive photoinitiator is linked to the base polymer by an anchor group, ie. a spacer. The spacer also serves to reduce the influence of the base polymer chain on the photochemical behavior of the initiator.

In principle, therefore, copolymerizable initiators have the following structure:

Scheme I

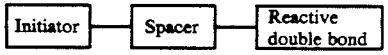

U.S. Pat. Nos. 3,214,492 and 3,429,852 describe acryloxy- or methacryloxy-substituted acetophenone and benzophenone derivatives, for example

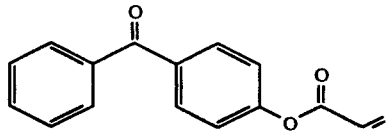

These can be copolymerized with ethylene or other vinyl monomers. This gives polymers which, for example after thermal deformation, are cured by irradiation. In the model according to Scheme I, the reactive double bond and the spacer are represented by the acryloxy group in these radiation-sensitive monomers.

In the 4-(4'-vinylbenzyloxy)-benzophenones

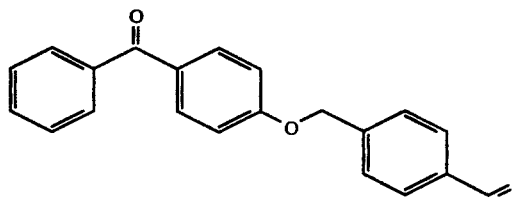

described in DE-A No. 28 18 763, this function is performed by the styrylbenzyloxy radical.

In Uvecryl ® P36, a commercial product from UCB, a particularly long spacer consisting of four ethyleneoxy units separates the benzophenone from the acryloxy radical.

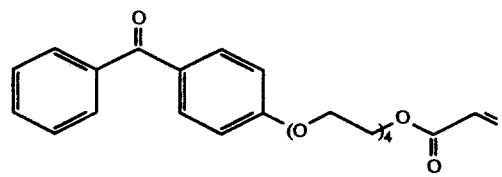

This compound, which is described in, for example, Technical Bulletin 2480/885 (1985) of UCB, can be used in photopolymers for coating materials. The synthesis is expensive.

The abovementioned patent literature shows that the ether or ester group is an important part of the spacer (cf. Scheme II).

Scheme II

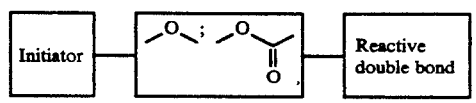

The ether or ester groups serve predominantly as linking elements between the spacer and the initiator fragment.

A novel structural scheme is obtained by considering the influence of the spacer as substituent on the photochemically excited acetophenone or benzophenone fragment. For example, possible spacers are those which can have a stabilizing or destabilizing effect because of their structures.

In particular, the carbamyl-substituted benzophenones of the type

Scheme III

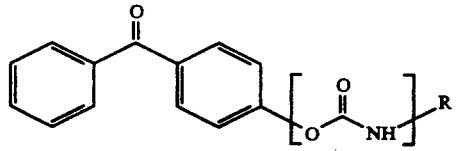

constitute an interesting class of substances from this point of view. U.S. Pat. No. 3,322,818 describes allyl-substituted and methallyl-substituted carbamylbenzophenones. However, they are only suitable as funicides (cf. Scheme IV).

Scheme IV

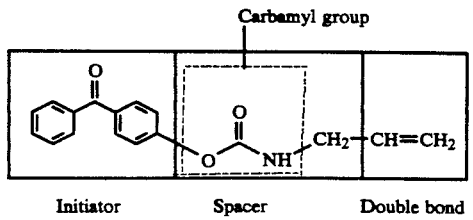

However, an allyl or methallyl group is not suitable for copolymerization These benzoylphenyl allylcarbamates are therefore of no practical importance in the polymer sector.

This applies to an even greater extent to the polyurethane UV stabilizers described in DE-A No. 20 31 477. Although these compounds contain a carbamyl group in the spacer, they have no reactive double bond.

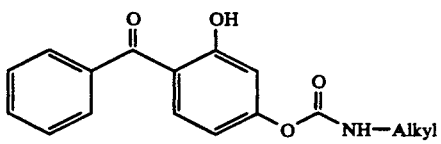

A photochemically interesting structure variant is described in EP-A No. 0 246 848. By reacting a reactive isocyanate with hydroxyethyloxyben-zophenone, a radiation-sensitive monomer having a particularly long spacer is obtained.

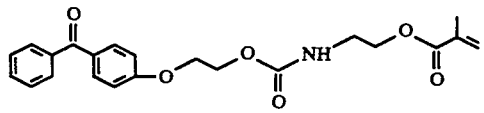

This monomer is copolymerizable but has the decisive disadvantage that the radiation-sensitive moiety of the molecule is bonded to the spacer via a photochemically only weakly activating ether group.

It is an object of the present invention to provide a radiation-sensitive, ethylenically unsaturated acetophenone or benzophenone derivative of a novel, previously unknown type, in which the carbamyl group is bonded directly to the initiator moiety and which additionally contains a reactive copolymerizable C—C double bond.

Scheme V

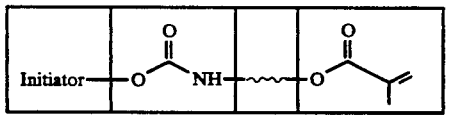

We have found that this object is achieved by ethylenically unsaturated copolymerizable, radiation-sensitive organic compounds of the general formula (I)

 (I)

where R is a straight-chain alkyl radical of 1 to 4 carbon atoms, preferably methyl, ethyl or n-propyl, an unsubstituted or substituted, branched alkyl radical of 3 or 4 carbon atoms, such as isopropyl, sec-hydroxyisopropyl or tert-butyl, aryl, such as phenyl, tolyl or naphthyl, or a radical $R^1$, and $R^1$ is a radical

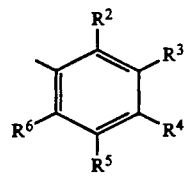

where $R^2$ to $R^6$ are identical or different and are each H, alkyl of 1 to 3 carbon atoms, eg. methyl, ethyl, n-propyl, isopropyl, OH, $OCH_3$, $OC_2H_5$, SH, $SCH_3$, $SC_2H_5$, Cl, F, $N(CH_3)_2$, $N(C_2H_5)_2$ or $N(CH_3)C_6H_5$, and not less than one but not more than three of the radicals $R_2$ to $R^6$ are each a radical

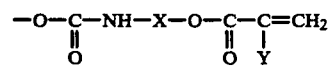

where X is a divalent alkylene radical —$(CH_2)_m$—, in which m is from 1 to 10, preferably ethylene, a perfluorinated alkylene radical —$(CF_2)_m$—, in which m is from 1 to 10, preferably perfluoroethylene, an oxaalkylene radical of the type —$(CH_2)_n$—O—$(CH_2)_p$—, in which n is from 1 to 5 and p is from 1 to 5, preferably n and p are each 2, ie.—$C_2H_4$—O—$C_2H_4$—, a perfluorinated oxaalkylene radical of the type —$(CF_2)_n$—O—$(CF_2)_p$—, in which n and p are each from 1 to 5, for example tetrafluoroethylene, or a polyoxaalkylene radical which may be perfluorinated and has 2 to 5 oxygen atoms, which are bonded to one another via one or more —$CH_2$— or —$CF_2$— groups, and Y is H or methyl.

Surprisingly, the novel compounds have particularly high photochemical reactivity in the medium-wavelength to relatively long-wavelength UV range.

It is a further object of the present invention to provide a process for the preparation of novel radiation-sensitive carbamylbenzophenones and carbamylacetophenones having one or more terminal methacrylate or acrylate groups.

The synthesis of aryl carbamates without a copolymerizable terminal group is known. A good overview is given by C. Ferri, Reaktionen der organischen Synthese, G. Thieme Verlag, Stuttgart, 1978.

The most important preparation process is the reaction of an aromatic alcohol with an isocyanate (cf. Houben-Weyl VIII, page 141; O. S. Petersen, Liebigs Ann. Chem. 562 (1947), 205; J. Burkus, J. Org. Chem. 26 (1961), 779; I. T. Kay and N. Punja, J. Chem. Soc., C 1968, 3011; and L. Capuano and R. Zander, Chem. Ber. 104 (1971), 2212). The carbamates are formed in good to very good yields if the alcohol and the isocyanate are reacted with one another in a molar ratio of 1:1 in the absence of a solvent or in excess alcohol as a solvent. Where the alcohol or the phenol is in the form of a solid, aprotic solvents, eg. dichloromethane, dichloroethane, acetonitrile, toluene, etc., are used.

When this preparation process is used for ω-isocyanatoalkyl (meth)acrylates of the general formula (II), where X is an alkylene radical which may be perfluorinated, an oxaalkylene radical or a polyoxaalkylene radical, each of 2 to 12 carbon atoms, and Y is H— or $CH_3$—, it has been found, surprisingly, that the desired carbamylbenzophenones containing (meth)acrylate groups are formed in a high, virtually quantitative yield. This is surprising in that acrylates or methacrylates can readily undergo many side reactions (crosslinking, polymerization).

The ω-isocyanatoalkyl (meth)acrylates required for the reaction of the hydroxyacetophenones or hydroxybenzophenones can be prepared in good yield by the process described in EP-A No. 083764 and DE-A No. 35 23 692.

The hydroxyacetophenones and hydroxybenzophenones required as further starting materials can be prepared by known processes. For example, 4-hydroxybenzophenone is obtained in about 90% yield by subjecting phenol to a Friedel-Crafts acylation with benzoyl chloride in nitrobenzene in the presence of $AlCl_3$ or $TiCl_4$ (Houben-Weyl 7/2a, page 186) or is obtained free of isomers by oxidation of 4-hydroxydiphenylmethane with 5,6-dichloro-2,3-dicyano-p-benzoquinone (Houben-Weyl 7/2a, page 681).

The present invention furthermore relates to a process for the preparation of compounds of the general formula (I), wherein a compound of the general formula (II)

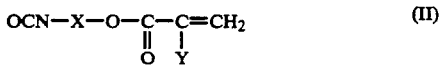
(II)

where X and Y have the abovementioned meanings, preferably, for example, isocyanatoethyl methacrylate or 5-isocyanato-3-oxapentyl methacrylate, is reacted with a compound of the general formula (III)

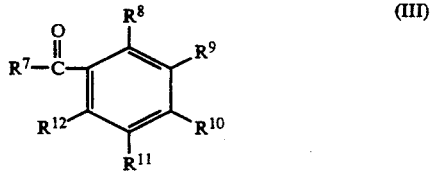
(III)

where $R^7$ is a straight-chain alkyl radical of 1 to 4 carbon atoms, preferably methyl, ethyl or n-propyl, an unsubstituted or substituted, branched alkyl radical of 3 or 4 carbon atoms, such as isopropyl, sec-hydroxyisopropyl or tert-butyl, or aryl, eg. phenyl, tolyl or naphthyl, preferably phenyl, and $R^8$ to $R^{12}$ are identical or different and are each H, alkyl of 1 to 3 carbon atoms, eg. methyl, ethyl, n-propyl or isopropyl, OH, $OCH_3$, $OC_2H_5$, SH, $SCH_3$, $SC_2H_5$, Cl, F, $N(CH_3)_2$, $N(C_2H_5)_2$ or $N(CH_3)C_6H_5$, with the proviso that one or more of the radicals $R^8$ to $R^{12}$ are hydroxyl, in an equimolar ratio or in two or three times this ratio, if necessary with not more than a 20% excess of the isocyanate, in the absence of moisture, in the presence or absence of an inert solvent or solvent mixture and of a basic catalyst, at from 0° to 100° C., preferably from 20° to 50° C.

Regarding the preparation process, the following may be stated specifically.

The isocyanates used in the reaction react readily with nucleophiles, including water. In the reaction, it is therefore essential to ensure strict absence of moisture by using dried nonnucleophilic solvents, eg. acetonitrile, dichloromethane, dichloroethane, tetrahydrofuran, toluene, chlorobenzene, ethyl acetate, chloroform, etc. and to maintain an inert gas atmosphere, for example nitrogen, argon or carbon dioxide.

As a rule, a solution of the hydroxy compound in an inert solvent, which may be omitted if the compound of the general formula (III) is liquid, is initially taken at from 0° to 100° C., preferably from 20° to 50° C. The liquid isocyanate is then added dropwise, while stirring. To initiate the reaction, a basic, nonnucleophilic amine, preferably triethylamine, 4-dimethylaminopyridine, 1,4-diazabicyclo[2.2.2]octane, 1,5-diazabicyclo[4.3.0]-non-5-ene, 1,8-diazabicyclo[5.4.0]undec-7-ene, polyvinylpyridine, etc., advantageously dissolved in an inert organic solvent, can then be added dropwise to this mixture at a rate such that the internal temperature can be kept below 100° C., preferably at from 20° to 50° C.

This procedure is very suitable for laboratory experiments.

For work on a larger scale, the synthesis is preferably carried out in the slightly modified manner below.

A compound of the general formula (III) and the amine in a inert solvent are initially taken in the absence of moisture at from 20° to 60° C., and the isocyanate, preferably without being diluted with a solvent, is added dropwise at a rate such that the internal temperature can be kept in the stated range.

After stirring has been carried out for a further 1-20 hours at from 10° to 30° C., the solvent is distilled off under reduced pressure until the weight of the residue remains constant. Crystalline products can additionally be readily recrystallized from an alcohol, eg. isopropanol.

The structure of all compounds stated in the Examples below was confirmed by $^1$H-NMR, IR and mass spectra.

EXAMPLE 1 p-N-(Methacryloylethyl)-carbamyloxyacetophenone

In a four-necked flask equipped with a stirrer, a reflux condenser, an internal thermometer and a dropping funnel, 20 ml of toluene were initially taken at room temperature and 3.5 g (25 millimoles) of 4-hydroxyacetophenone and 4.25 g (27.5 millimoles) of isocyanatoethyl methacrylate were dissolved therein. 0.2 g (2 millimoles) of triethylamine in 10 ml of tetrahydrofuran was then added dropwise at an internal temperature of 20°-26° C., and stirring was continued for 2 hours at room temperature. After the addition of a fairly small amount of phenothiazine, the solvent was distilled off under reduced pressure from a water pump and the residue was recrystallized from isopropanol.

Yield: 6.1 g (84%) of virtually colorless crystal. Mp. 87°-88° C.

EXAMPLE 2 p-N-(Methacryl-4-oxapentamethylene)-carbamyloxyacetophenone

The synthesis was carried out similarly to the method stated in Example 1. The following amounts were used:
3.4 g (25 millimoles) of 4-hydroxyacetophenone, 20 ml of toluene,
5.5 g (27.5 millimoles) of 5-isocyanato-3-oxapentyl methacrylate and
0.2 g (2 millimoles) of triethylamine.
Yield: 8.2 g (98%) of yellowish oil.

EXAMPLE 3 p-N-(Methacryloyl-4-oxapentamethylene)-carbamyloxybenzophenone

Method 1

109.5 g (0.55 mole) of 5-isocyanato-3-oxapentamethylene methacrylate and 99 g (0.5 mole) of 4-hydroxybenzophenone in 90 ml of toluene were initially taken at room temperature, and a solution of 2.1 g of triethylamine in 75 ml of tetrahydrofuran was slowly added dropwise at 20°-25° C. (slight cooling required). During this procedure, the internal temperature increased to about 40° C. The reaction mixture was left to stand for 12 hours, after which it had cooled to room temperature, 100 mg of phenothiazine were then added and the mixture was evaporated down to constant weight in a rotary evaporator under reduced pressure from an oil pump, at a bath temperature of not more than 35° C.

Yield: 197 g (quantitative) of a honey-colored, viscous oil.

Method 2

90 kg (0.5 kilomoles) of 4-hydroxybenzophenone were dissolved in a mixture of 90 l of anhydrous toluene and 125 l of dry tetrahydrofuran at from 20° to 30° C. Thereafter, 3.5 kg of triethylamine were added, while stirring. 109.5 kg (0.55 kilomole) of 5-isocyanato-3-oxa-pentyl methacrylate were metered in at an internal temperature of 20° to 25° C. at a rate such that the internal temperature did not exceed 30° C. Stirring was continued for 12 hours at 20° to 25° C., after which 100 g of phenothiazine were added and the solvent mixture was distilled off to a maximum bath temperature of 35° C. under about 10–15 mbar.

Yield: 198 kg (quantitative).

EXAMPLES 4–8

Further functionalized isocyanates can be reacted with hydroxybenzophenones by the method described in Example 3. The following reactions are Examples:

EXAMPLE 9

Naphthyl 2-acetyl-4-ethyl-7-methoxy-1-N-(methacryloylethylene)-carbamate 12.2 g (50 millimoles) of 2-acetyl-4-ethyl-7-methoxy-1-naphthol and 8.6 g (55 millimoles) of isocyanatoethyl methacrylate in 50 ml of dry toluene were initially taken and 0.5 g of triethylamine in 15 ml of tetrahydrofuran was added dropwise in the course of minutes. Stirring was carried out for 52 hours at room temperature, after which the precipitated crystals were filtered off under suction, washed with toluene and dried under reduced pressure.

Yield: 11 g (53%) of colorless crystals.
Mp.: 124°–126° C. (decomposition).

EXAMPLE 10

The 4-carbamic ester of methyl 3-benzoyl-4-hydroxy-6-methoxy-1-naphthylacetate could be prepared in 64% yield by reaction with isocyanatoethyl methacrylate, similarly to the synthesis of the compound described in Example 9.

Mp. 147°–148° C. (decomposition).

EXAMPLE 11

4,4'-Bis-((N-methacryloxyethyl)-carbamyloxy)-benzophenone 34.2 (0.22 mole) of isocyanatoethyl methacrylate and 22 g (0.1 mole) of 4,4'-bishydroxybenzophenone were dissolved in 300 ml of toluene in the absence of moisture, and a solution of 0.7 g of triethylamine in 50 ml of

| Example | Isocyanate (1.2 mole) | Benzophenone (1 mole) | Yield [%] | Mp. |
| --- | --- | --- | --- | --- |
| 4 | methacrylate-O-CH2CH2-NCO | 4-hydroxy-benzophenone | 81 | 101–102° C. |
| 5 | methacrylate-O-CH2CH2-NCO | 2-hydroxy-benzophenone | 98 | yellow oil |
| 6 | methacrylate-O-CH2CH2-NCO | 2,4-dihydroxy-benzophenone | 85* | yellowish oil |
| 7 | methacrylate-O-CH2CH2-O-CH2CH2-NCO | 2-hydroxy-benzophenone | 98 | yellow oil |
| 8 | methacrylate-O-CH2CH2-O-CH2CH2-NCO | 2,4-dihydroxy-benzophenone | 90* | yellow oil |

In the acetophenone or benzophenone moiety of the carbamates too, the substituents can be varied.

tetrahydrofuran was added dropwise at room temperature. The exothermic reaction was kept at 28°–30° C. by cooling in an ice bath, and stirring was continued for 10 hours at room temperature. The precipitated crystals were washed with toluene, dried, and recrystallized from isopropanol.

Yield: 43 g (82%) of virtually colorless crystals of melting point 135°-136° C.

EXAMPLE 12

The less reactive 4,4'-bis-(p-hydroxyphenyleneoxy)-benzophenone can also be converted into the carbamic ester as described in Example 11. No exothermic reaction is observed and the reaction mixture is left to stand for 72 hours at room temperature before being worked up. The toluene filtrate is evaporated down under reduced pressure from an oil pump and the residue is recrystallized from isopropanol.

Yield: 64%.

Mp.: decomposition above 140° C. (complete decomposition at 270° C.)

Analysis (Example 12): Calculated: C 66.1 . H 5.09, N 3.95. Found: 66.2, 5.2, 3.9.

EXAMPLE 13

N-(Benzoyl-p-phenylene)-N,-(methacryloxyethylene)-carbodiimide 8.5 g (55 millimoles) of isocyanatoethyl methacrylate and 9.8 g (50 millimoles) of 4-aminobenzophenone in 50 ml of toluene were initially taken in the absence of moisture. 0.7 g of triethylamine in 15 ml of tetrahydrofuran was added, after which the mixture was stirred for 15 hours at 55° C., cooled, and then evaporated down under reduced pressure from a water pump. The oily residue was triturated with acetone/petroleum ether and the resulting crystals were crystallized from isopropanol with the addition of a small amount of phenothiazine.

Yield: 12 g (68%) of colorless crystals of melting point 134°-137° C.

EXAMPLE 14

4'-Dimethylamino-4-(N-(methacryloylethyl)-carbamyloxy)benzophenone 0.35 g of triethylamine, dissolved in 13 ml of tetrahydrofuran, was added dropwise at from 15° to 20° C. to a solution of 11.6 g (50 millimoles) of 4-hydroxy-4'-dimethylaminobenzophenone and 8.6 g (55 millimoles) of isocyanatoethyl methacrylate in 50 ml of toluene. The temperature was found to increase slightly to about 30° C. After stirring had been carried out for 10 hours at room temperature, the precipitated crystals were filtered off under suction, washed with toluene and recrystallized from isopropanol.

Yield: 16.5 g (83%) of colorless crystals of melting point 127°-130° C.

EXAMPLE 15

4-Dimethylamino-4'-(N-(methacryloyl-4-oxapentamethylene)-carbamyloxy)-benzophenone The compound was prepared similarly to Example 12 and a corresponding amount of 11 g (55 millimoles) of 5-isocyanato-3-oxapentyl methacrylate was used.

Yield: 22 g (quantitative) of a pale yellow oil.

We claim:

1. An ethylenically unsaturated copolymerizable radiation-sensitive organic compound of the formula (I)

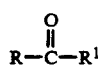
(I)

where R is a straight-chain alkyl radical of 1 to 4 carbon atoms, an unsubstituted or hydroxy substituted, branched alkyl radical of 3 to 4 carbon atoms, aryl or a radical $R^1$, and $R^1$ is a radical

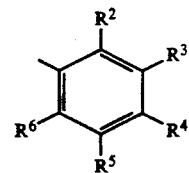

where $R^2$ to $R^6$ are identical or different and are each H, alkyl of 1 to 3 carbon atoms, $OCH_3$, $OC_2H_5$. $N(CH^3)_2$, $N(C_2H_5)_2$ or $N(CH_3)C_6H_5$, and not less than one but not more than three of the radicals $R^2$ to $R^6$ are each a radical

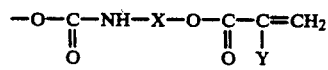

where X is a divalent alkylene radical $—(CH_2)_m—$ in which m is from 1 to 10, an oxaalkylene radical of the formula $—(CH_2)_n—O—(CH_2)_p—$ in which n is from 1 to 5 and p is from 1 to 5, or a polyoxaalkylene having 2 to 12 carbon atoms and 2 to 5 oxygen atoms which are bonded to one another by one or more $—CH_2—$ groups and Y is H or methyl.

2. A process for the preparation of a compound of the formula (I) as defined in claim 1, wherein a compound of the formula (II)

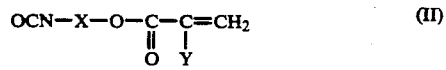
(II)

where X and Y have the meanings stated in claim 1, is reacted with a compound of the formula III

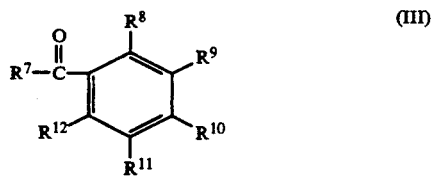
(III)

where $R^7$ is a straight-chain alkyl radical of 1 to 4 carbon atoms, an unsubstituted or hydroxy substituted, branched alkyl radical of 3 or 4 carbon atoms or aryl, and $R^8$ to $R^{12}$ are identical or different and are each H, alkyl of 1 to 3 carbon atoms, $OCH_3$, $OC_2H_5$, $N(CH_3)_2$, $N(C_2H_5)_2$ or $N(CH_3)C_6H_5$, with the proviso that one or more of the radicals $R^8$ to $R^{12}$ are hydroxyl, in an equimolar ratio or in two or three times this ratio, in the presence or absence of an inert solvent or solvent mixture and of a basic catalyst, at from 0° to 100° C. under anhydrous conditions.

3. A process as defined in claim 2, wherein the compound of the formula (II) is an ω-isocyanatoalkyl (meth)acrylate.

4. A process as defined in claim 2, wherein from 1 to 1.2 moles of the isocyanate of the formula (II) are reacted per mole of the compound of the formula (III).

5. A process a in claim 3, wherein from 1 to 1.2 moles of the of the formula (II) are reacted per mole of the compound of the formula (III).

6. A process as defined in claim 2, wherein not less than a catalytic amount of a strong, nonnucleophilic base, is present.

7. A process as defined in claim 3, wherein not less than a catalytic amount of a strong, nonnucleophilic base, is present.

8. A process as defined in claim 4, wherein not less than a catalytic amount of a strong, nonnucleophilic base, is present.

9. A process as defined in claim 2, wherein the reaction temperature is from 20° to 50° C.

10. A process as defined in claim 2, wherein the procedure is carried out in an inert, anhydrous solvent in the absence of moisture.

11. The process of claim 6, wherein the strong, nonnucleophilic base is an amine.

12. The process of claim 7, wherein the strong, nonnucleophilic base is an amine.

13. The process of claim 8, wherein the strong, nonnucleophilic base is an amine.

14. An ethylenically unsaturated copolymerizable radiation-sensitive organic compound of the formula I

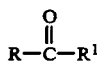
(I)

where R is a straight-chain alkyl radical of 1 to 4 carbon atoms, an unsubstituted or hydroxy substituted, branched alkyl radial of 3 to 4 carbon atoms, aryl or a radical $R^1$, and $R^1$ is a radical

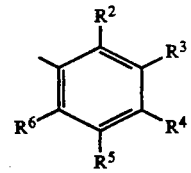

where $R^2$ to $R^6$ are identical or different and are each H, alkyl of 1 to 3 carbon atoms, $OCH_3$, $OC_2H_5$, $N(CH_3)_2$, $N(C_2H_5)_2$ or $N(CH_3)C_6H_5$, and not less than one but not more than three of the radicals $R^2$ to $R^6$ are each a radical

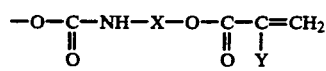

where X is a divalent alkylene radical —$(CH_2)_m$— and in which m is from 1 to 10, an oxaalkylene radical of the formula —$CH_2)_n$—O—$(CH_2)_p$— in which n is from 1 to 5 and p is from 1 to 5, or a polyoxaalkylene radical which has 2 to 5 oxygen atoms which are bonded to one another by one —$CH_2$— group and Y is H or methyl.

* * * * *